US012754187B2

(12) United States Patent
Seelig et al.

(10) Patent No.: US 12,754,187 B2
(45) Date of Patent: Oct. 6, 2026

(54) METHODS FOR PROTEIN IDENTIFICATION THROUGH COMBINATORIAL BARCODING

(71) Applicant: University of Washington, Seattle, WA (US)

(72) Inventors: Georg Seelig, Seattle, WA (US); Sergeii Pochekailov, Seattle, WA (US); Peter J. Matulich, Seattle, WA (US)

(73) Assignee: University of Washington, Seattle, WA (US)

( * ) Notice: Subject to any disclaimer, the term of this patent is extended or adjusted under 35 U.S.C. 154(b) by 565 days.

(21) Appl. No.: 18/258,474

(22) PCT Filed: Feb. 7, 2022

(86) PCT No.: PCT/US2022/015473

§ 371 (c)(1),
(2) Date: Jun. 20, 2023

(87) PCT Pub. No.: WO2022/173690

PCT Pub. Date: Aug. 18, 2022

(65) Prior Publication Data

US 2024/0044908 A1 Feb. 8, 2024

Related U.S. Application Data

(60) Provisional application No. 63/147,669, filed on Feb. 9, 2021.

(51) Int. Cl.
*G01N 33/68* (2006.01)
*G01N 33/58* (2006.01)

(52) U.S. Cl.
CPC ......... *G01N 33/6803* (2013.01); *G01N 33/58* (2013.01)

(58) Field of Classification Search
CPC ............... G01N 33/6803; G01N 33/58; G01N 2458/10; C12Q 1/68
See application file for complete search history.

(56) References Cited

U.S. PATENT DOCUMENTS

| | | | |
|---|---|---|---|
| 2016/0138086 | A1 | 5/2016 | Seelig et al. |
| 2019/0144854 | A1 | 5/2019 | Ismagilov et al. |
| 2019/0187156 | A1 | 6/2019 | Quinodoz et al. |
| 2020/0348308 | A1 | 11/2020 | Chee et al. |

OTHER PUBLICATIONS

International Search Report mailed on Apr. 26, 2022, issued in the corresponding International App. No. PCT/US2022/015473, filed on Feb. 7, 2022, 2 pages.

Written Opinion of the International Searching Authority mailed on Apr. 26, 2022, issued in the corresponding International App. No. PCT/US2022/015473, filed on Feb. 7, 2022, 5 pages.

Zhang, Y. et al., "Detecting protein and post-translational modifications in single cells with iDentification and qUantification sEparaTion (DUET)," Communications Biology (2020) 3:420 | https://doi.org/10.1038/s42003-020-01132-8 <www.nature.com/commsbio>.

*Primary Examiner* — Cynthia B Wilder
(74) *Attorney, Agent, or Firm* — Christensen O'Connor Johnson Kindness, PLLC

(57) ABSTRACT

Methods and kits for assessing and partially or uniquely identifying proteins, such as in complex mixtures of proteins and other molecules/structures, are described. In an embodiment, the methods include combinatorially barcoding target amino acid residues on the protein and, in certain embodiments, enzymatically cleaving the protein, such as before and after rounds of combinatorial barcoding. In an embodiment, the methods include (a) attaching a first nucleic acid molecule to target amino acid residues in the plurality of proteins in the sample to provide nascent nucleic acid tags at the target amino acid residues; (b) performing one or more rounds of split-pool barcoding to provide mature nucleic acid tags at the target amino acid residues (c) sequencing the mature nucleic acid tags; and (d) determining a frequency of the target amino acid residues in one or more protein of the plurality of proteins.

20 Claims, 11 Drawing Sheets

DNA barcodes sequenced
represent history of protein molecules

Branching points indicate protease activities

METHODS FOR PROTEIN IDENTIFICATION THROUGH COMBINATORIAL BARCODING

CROSS-REFERENCE TO RELATED APPLICATION

This application is a U.S. national phase application of International Application No. PCT/US2022/015473, filed on Feb. 7, 2022, which claims the benefit of U.S. Provisional Application No. 63/147,669, filed Feb. 9, 2021, each of which are hereby incorporated by reference in entirety.

BACKGROUND

Each cell contains thousands of distinct proteins with abundances varying from just a few to millions. Directly measuring the cellular proteome at the single-cell level would provide a detailed readout of cell state and function. Reliable methods for protein identification could also revolutionize antibody discovery and other areas of protein engineering. Currently, mass spectrometry and, to a lesser extent, peptide sequencing based on Edman chemistry are the work horses of protein identification. However, these approaches require large amounts of proteins and cannot detect low-abundance proteins.

Recent approaches to single-molecule protein sequencing are beginning to address this limitation but generally require sophisticated instrumentation, have limited throughput and, to the extent that they have been implemented experimentally at all, can only be used to sequence short peptides.

Accordingly, there is presently a need to provide methods and kits for partially or uniquely identifying proteins and corresponding protein sequences in complex mixtures of proteins, such as from a biological sample, quickly and with inexpensive and widely available reagents and instruments.

SUMMARY

The present disclosure addresses these and related challenges by providing kits and methods for assessing and partially or uniquely identifying proteins, such as in complex mixtures of proteins and other molecules/structures.

Accordingly, in an aspect, the present disclosure provides a method of assessing target amino acid residue frequency and/or number in a plurality of proteins in a sample. In an embodiment the method comprises (a) attaching a first nucleic acid molecule to target amino acid residues in the plurality of proteins in the sample to provide nascent nucleic acid tags at the target amino acid residues; (b) performing one or more rounds of split-pool barcoding to provide mature nucleic acid tags at the target amino acid residues, wherein the one or more rounds of split-pool barcoding comprise: (i) splitting the sample into a plurality of partitions, (ii) ligating a barcode nucleic acid molecule to the first nucleic acid molecules attached to the proteins, wherein the barcode nucleic acid molecule in each partition in the plurality of partitions comprise a barcode sequence unique to that partition, and (iii) pooling the sample; (c) sequencing the mature nucleic acid tags; and (d) determining a frequency of the target amino acid residues in one or more protein of the plurality of proteins.

In another aspect, the present disclosure provides a kit for assessing, analyzing, fingerprinting, and/or identifying proteins, such as proteins in a complex mixture or sample. In an embodiment, the kits are configured for and useful in performing one or more of the methods of the present disclosure. In an embodiment, the kit comprises a functional group configured to couple with or covalently bind to a target amino acid residue. In an embodiment, the kit further comprises a first nucleic acid configured to react with and couple to the functional group. In an embodiment, the kit further comprises one or more barcode nucleic acid molecules. In an embodiment, the barcode nucleic acid molecules are configured to hybridize with, bind to, or otherwise couple with the first nucleic acids, such as to form mature nucleic acid tags through one or more rounds of split-pool barcoding. In an embodiment, the kit further comprises one or more beads or particles.

In an embodiment, the kit comprises a functional group configured to couple with or covalently bind to a target amino acid residue; a first nucleic acid configured to react with and couple to the functional group; one or more barcode nucleic acid molecules configured to hybridize with, bind to, or otherwise couple with the first nucleic acids; and a chemical cleavage agent configured to cleave a protein.

This summary is provided to introduce a selection of concepts in a simplified form that are further described below in the Detailed Description. This summary is not intended to identify features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

Figure 1:
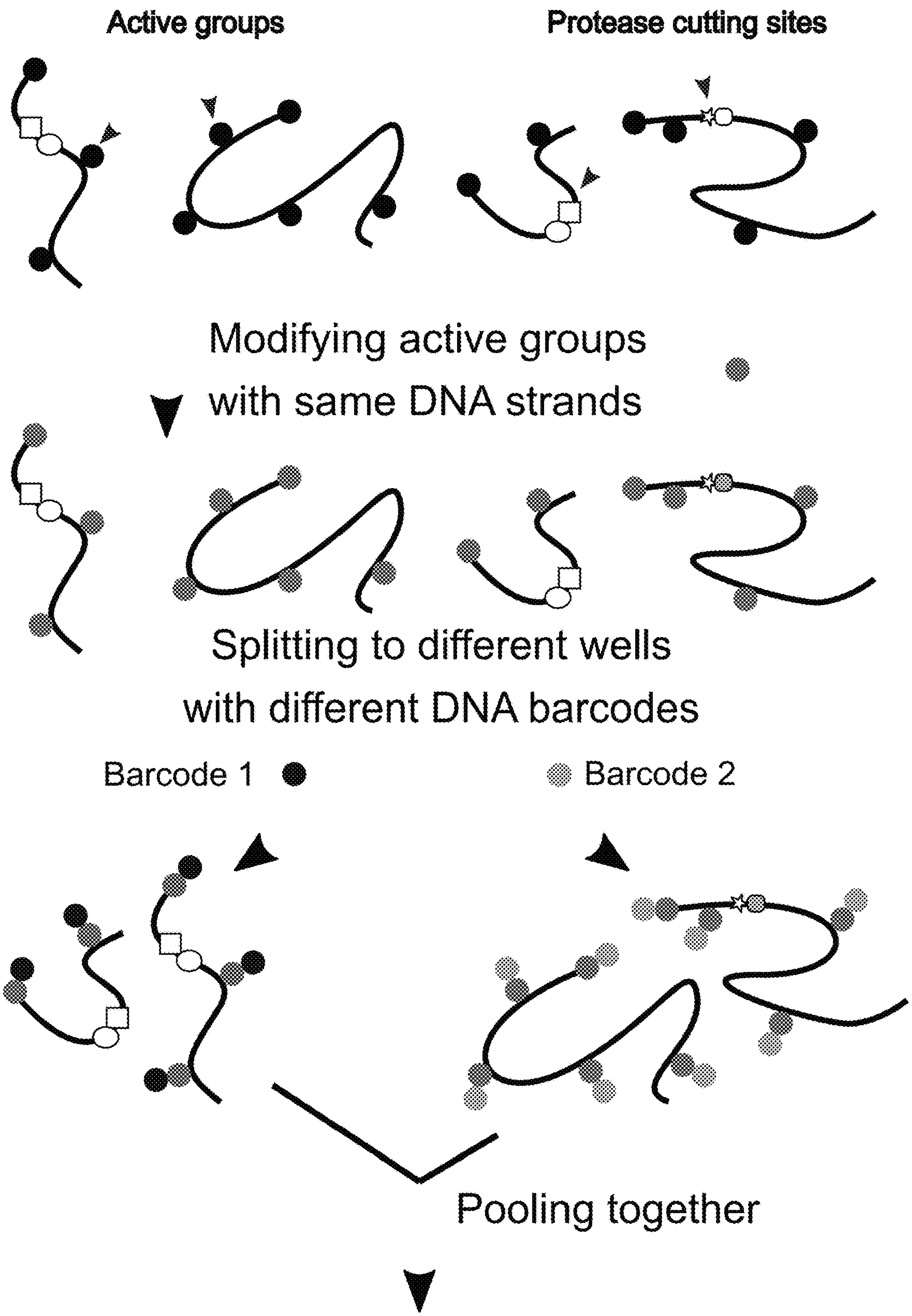
FIG. 1 schematically illustrates a method of combinatorially labelling proteins, according to an embodiment of the present disclosure.
Figure 1:
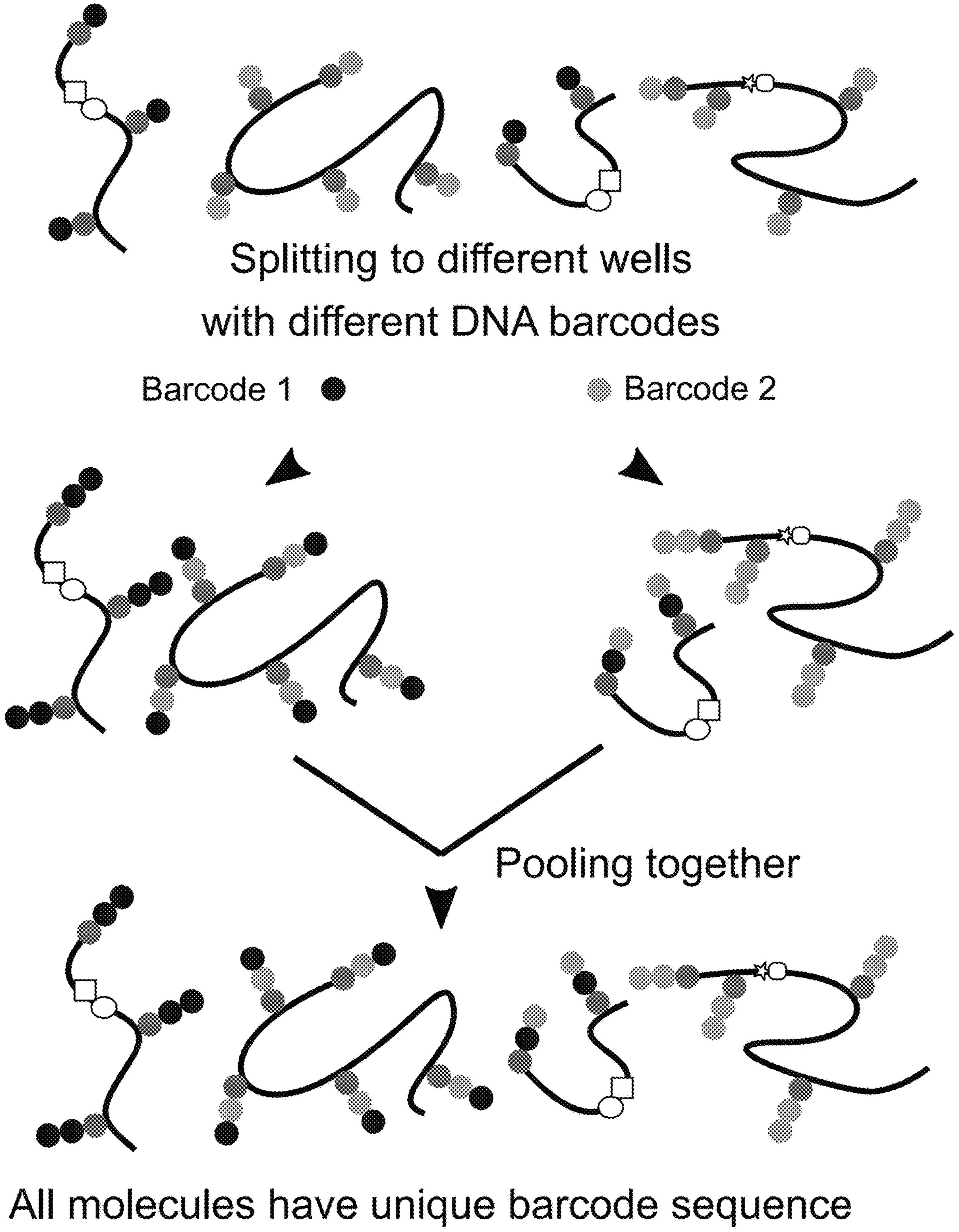

The present disclosure provides, in various aspects, methods and kits for assessing or analyzing proteins, such as in a complex mixture including proteins.

Methods

In an aspect, the present disclosure provides methods for assessing and partially or uniquely identifying proteins, such as in complex mixtures of proteins and other molecules/structures, through combinatorially barcoding target amino acid residues on the protein and, in certain embodiments, enzymatically or chemically cleaving the protein, such as before and after rounds of combinatorial barcoding.

As described in greater detail herein, in an embodiment, the methods of the present disclosure are configured to assess a frequency and/or number of target amino acids within a protein. In an embodiment, the methods of the present disclosure are also configured to fingerprint or uniquely identify proteins within a sample, such as a complex mixture. In an embodiment, fingerprinting a protein refers to identifying or narrowing protein identity possibilities based on certain structural or sequence features of a protein, such as target amino acid number and/or a number of specific amino acid sequences within the protein. Such fingerprinting may be based on partial protein composition information or other protein structural or sequence information, rather than complete protein sequence information.

As described further herein, the methods of the present disclosure provide a number of advantages over conventional methods of protein sequencing, identification, fingerprinting, and the like. These advantages include, but are not limited to, the following identified advantages. (1) The methods of the present disclosure are massively parallel. In this regard, throughput is limited only by the number of barcode combinations that can be generated. For example, using 4 rounds of combinatorial barcoding according to the methods of the present disclosure in a 384-well plate format would generate over 20 billion barcode combinations, enough to uniquely barcode and fingerprint 200 million proteins with a 1% error rate. (2) Because it is not necessary to manipulate individual proteins, an entire experiment can be performed using standard laboratory equipment, such as with multi-well plate, pipettes, and the like, and without the need for complex instrumentation, such as nanopore sequencers or single-molecule fluorescence microscopes. Instead, identifying information, such as barcode nucleic acid molecules, is appended to the entity of interest through a repeated process of splitting (e.g., into a 96-well plate), barcoding (e.g., adding a DNA sequence unique to a well to all cell/molecules in that well) and pooling (mixing all the barcoded entities back together). (3) The methods of the present disclosure convert the extremely challenging problem of protein identification into the solved problem of DNA sequencing, thus overcoming fundamental limitations of direct protein sequencing assays. (4) The methods of the present disclosure are not limited to short peptides but are instead also well-suited for the analysis of full-length proteins.

In an embodiment, the methods of the present disclosure are methods for assessing target amino acid residue frequency and/or number in a plurality of proteins in a sample, the methods comprising: (a) attaching a first nucleic acid molecule to target amino acid residues in the plurality of proteins in the sample to provide nascent nucleic acid tags at the target amino acid residues; (b) performing one or more rounds of split-pool barcoding to provide mature nucleic acid tags at the target amino acid residues, wherein the one or more rounds of split-pool barcoding comprise: (i) splitting the sample into a plurality of partitions, (ii) ligating a barcode nucleic acid molecule to the first nucleic acid molecules attached to the proteins, wherein the barcode nucleic acid molecule in each partition in the plurality of partitions comprise a barcode sequence unique to that partition, and (iii) pooling the sample; (c) sequencing the mature nucleic acid tags; and (d) determining a frequency of the target amino acid residues in one or more protein of the plurality of proteins.

In an embodiment, the sample includes a mixture of a number of different proteins. In an embodiment, the sample is a biological sample derived from a subject. In an embodiment, the biological sample is selected from the group consisting of saliva, whole blood, blood plasma, mucus, cerebrospinal fluid, lymph, sweat, tears, stool, urine, pus, tissue, bone, and combinations thereof. In an embodiment, the sample is a purified, filtered, or otherwise altered sample that has been manipulated to concentrate proteins and/or remove portions of an original sample, such as to remove non-proteinaceous components. In an embodiment, the sample comprises proteins from a single cell, such as a single cell that has been digested or otherwise manipulated to provide proteins formerly contained therein. In an embodiment, the sample comprises proteins from a tissue sample, such as a tissue sample that has been digested or otherwise manipulated to provide proteins formerly contained therein. In an embodiment, the sample derived from an animal subject, such as a human subject.

Functionalization and Groups

As above, in an embodiment, the method includes attaching a first nucleic acid molecule to target amino acid residues in the plurality of proteins in the sample to provide nascent nucleic acid tags at the target amino acid residues.

The target amino acid residues can include any amino acids, including canonical and non-canonical amino acids. In an embodiment, the target amino acid residues include reactive amino acids, such as amino acids including one or more reactive side chains. In an embodiment, the target amino acid residues are selected from the group consisting of lysine, glutamic acid, aspartic acid, cysteine, arginine, histidine, tyrosine, and combinations thereof. In an embodiment, the target nucleic acid residues comprise sidechain groups selected from the group consisting of an amine group, a carboxylic acid group, a thiol group, unnatural amino acid reactive residues and combinations thereof.

In an embodiment, the target amino acid residues comprise amino-groups (—$NH_2$), that occur on lysines, the N-terminus of a protein, or appears as a result of a post-translational modification, either natural or artificial. In an embodiment, the target amino acid residues comprise thiol groups, either in oxidized (—S—S—) or reduced form (—S—H). In an embodiment, the thiol groups occur as part of cysteine amino acid, or as a result of a post-translational modification, either natural or artificial. In an embodiment, the target amino acid residues comprise carboxyl groups (—COOH), that occurs at aspartic or glutamic acids, or at the C-terminus of a protein, or as a result of a post-translational modification, either natural or artificial. In an embodiment, the target amino acid residues comprise any other active group that is contained in non-natural amino acids, which may be introduced to the protein structure. In an embodiment, the target amino acid residues comprise any amino acid or sequence of amino acids that may trigger an enzymatic reaction of covalent attachment (including, but not limited to SNAP tag, CLIP tag, etc.). In an embodiment, functionalizing the target amino acid residues does not include covalent interaction, but can include a strong non-covalent interaction between protein and DNA (Zn fingers, etc.).

In an embodiment, attaching the first nucleic acid molecule to the target amino acid residues in the plurality of proteins in the sample comprises coupling a functional group to the target amino acid residues. In an embodiment, the nascent nucleic acid tag includes the functional group. As used herein, the term "functional group" refers to any chemical unit that can be attached, such as by any stable physical or chemical association, to the target amino acid, thereby rendering the target amino acid available for conjugation. Non-limiting examples of functional groups include, carboxylic acid, amino, mercapto, azido, alkyne, aldehyde, hydroxyl, carbonyl, sulfate, sulfonate, phosphate, cyanate, succinimidyl ester, alkyne, strained alkyne, azide, diene, alkene, cyclooctyne, isothiocyanate, and phosphine groups, substituted derivatives thereof, and combinations thereof.

In an embodiment, such as where the target amino acid residue comprises a reactive amine group, such as lysine, the functional group comprises an N-Hydroxysuccinimide (NHS) moiety. As described further herein, the NHS moiety or group is configured to covalently bond with amino groups, such as through click chemistry. In an embodiment, the functional group comprises an NHS group reactive to amino acid amine groups, and a dibenzocyclooctyne, or other group, reactive to azide groups.

In an embodiment, lysines are labelled using NHS esters. In an embodiment, cysteines are labelled using maleimide and/or iodoacetamide reactive groups. In an embodiment, a phenol ring of tyrosines can be labeled using benzyl diazo groups. In an embodiment, labelling can include selectively targeting tyrosine side chains is an ene-like reaction with cyclic diazodicaboxamides in aqueous buffer. In an embodiment, labelling carboxylic acid moieties, such as in aspartate and glutamate, includes standard technique (EDC coupling) for binding amines covalently to carboxylic acids, forming an amide bond. In an embodiment, tryptophan can be labeled at the C2 position using sulfenyl chlorides. In an embodiment, methionine, for example, can either be labeled with hypervalent iodine reagents or by the use of urea-derived oxaziridines.

In an embodiment, coupling a target amino acid to a nucleic acid molecule includes the use of a heterobifunctional linker. In an embodiment, the heterobifunctional linker includes a reactive group selected from the group consisting of (NHS) ($(CH_2CO)_2NOH$), maleimide ($H_2C_2(CO)_2NH$), azide ($N_3$), alkyne-derivatives, and combinations thereof.

In an embodiment, various chemistries may be used to couple the heterobifunctional linker to a nucleic acid, such as chemistries selected from the group consisting of azide-alkyne based chemistry; maleimide-thiol based chemistry, NHS-amine based chemistry, and combinations thereof.

In an embodiment, the NHS group is coupled to the dibenzocyclooctyne group through a linker, such as through a poly(ethylene glycol) (PEG) linker. In an embodiment, such azide-reactive moieties, such as dibenzocyclooctyne, are used to couple with azide-functionalized nucleic acid barcode molecules.

In an embodiment, active groups, such as in a heterobifunctional linker, are directly coupled. In an embodiment, active groups, such as in a heterobifunctional linker, are coupled through an alkyl linker.

While heterobifunctional linkers are described, it will be understood that homo-bifunctional linkers can be used, bearing the same active group at each end. In this case, the reaction is done in one stage, mixing protein, DNA adapter and linker together at the same time.

In an embodiment, attaching the first nucleic acid molecule to the target amino acid residues in the plurality of proteins in the sample comprises coupling the first nucleic acid to the functional group. In an embodiment, the nascent nucleic acid tag includes the functional group and the first nucleic acid. In an embodiment, the first nucleic acid comprises an azide group, such as an azide group configured to bond with an azide-reactive group of the first nucleic acid molecule, such as dibenzocyclooctyne.

While particular functional groups, target amino acid residues, and sidechain functional groups are specifically described, it will be understood that others are compatible with and within the scope of the methods of the present disclosure.

In an embodiment, the methods of the present disclosure include attaching a nucleic acid molecule to two or more sets of target amino acids in proteins. In this regard, the methods of the present disclosure are configured to barcode, such as combinatorially barcode, two or more sets of target amino acids. Such an approach may be configured to combinatorially barcoding two or more sets of target amino acids in a protein. For example, different types of target amino acids may be separately and differently barcoded to provide additional barcoding parameters, which may be used to fingerprint or otherwise identify barcoded proteins.

Accordingly, in an embodiment, the target amino acid residues are first target amino acid residues comprising first sidechain groups and the functional group is a first functional group, wherein the method further comprises attaching a second nucleic acid molecule to second target amino acid residues different than the first target nucleic acid in the plurality of proteins in the sample. In an embodiment, attaching a second nucleic acid molecule to second target amino acid residues comprises coupling a second functional group to the second target amino acid residues, and coupling the second nucleic acid to the second functional group. In an embodiment, the second functional groups include moieties or groups or are examples of the functional groups described elsewhere herein.

In an embodiment, the second functional groups do not react with the first target amino acids, and, correspondingly, the first functional groups do not react with the second target amino acids. In this regard, in an embodiment, a reaction between the first functional group and the first target amino acid residues is orthogonal to a reaction between the second functional group and the second target amino acid residues. In certain embodiments, an orthogonally reactive chemical group is a chemical group that reacts only with its designated chemical reactive group, but not with another chemical reactive group that may be present. For example, reactive groups A and B can form a designated pair that reacts with each other, and reactive groups Y and Z can form another designated pair that reacts with each other. In such embodiments, reactive group A is considered to be orthogonal with respect to Y because A does not react with Z, and reactive group Y is orthogonal with respect to A because Y does not react with B.

Such orthogonality is suitable to differently label or barcode the first and second target amino acid residues. If the reactions were not orthogonal, it may be difficult or even impossible to distinguish between the barcoded or labelled first and second target amino acids, making fingerprinting or identification of the labelled proteins correspondingly more challenging.

In an embodiment, the proteins are denatured. Such denaturing can include contacting the proteins with urea, sodium dodecyl sulfate (SDS), combinations thereof, or with other known protein-denaturing agents. If the proteins are not denatured, only surface residues may be labeled. In an embodiment, only surface proteins are labelled, such as where the protein is not denatured, such as to label and subsequently identify/fingerprint surface proteins, which may be useful in identifying surface proteins or entire proteins in combination with structural models.

In an embodiment, attaching the first nucleic acid molecule to target amino acid residues in the plurality of proteins in the sample, such as through coupling a functional group to the target amino acid residues, includes attaching the first nucleic acid molecule to every target amino acid residue in a protein. In an embodiment, attaching the first nucleic acid molecule to target amino acid residues in the plurality of proteins in the sample, such as through coupling a functional group to the target amino acid residues, attaches the first nucleic acid molecule to only a portion of the target amino acid residues, such as only 50%, 60%, 70%, 75%, 80%, 85%, 90%, 95%, 96%, 97%, 98%, 99%, or less than 100% of the target amino acid residues in the protein.

Split-Pool Barcoding

As above, in an embodiment, the methods of the present disclosure comprise one or more rounds of split-pool barcoding, such as to provide mature nucleic acid tags at or coupled to the target amino acid residues. In an embodiment, split-pool barcoding comprises (i) splitting the sample into a plurality of partitions, (ii) ligating a barcode nucleic acid molecule to a first nucleic acid molecules attached to the proteins, wherein the barcode nucleic acid molecule in each partition in the plurality of partitions comprise a barcode sequence unique to that partition, and (iii) pooling the sample.

As described further herein, such split-pool barcoding, especially repeated split-pool barcoding, is suitable to uniquely label target nucleic acid residues with a combinatorially generated nucleic acid tag, such as a mature nucleic acid tag or barcode. Examples of split-pool barcoding can be found, for example, in U.S. patent application Ser. No. 14/941,433, which is incorporated herein by reference in its entirety.

Splitting the sample can include separating the sample into a plurality of different portions, such as portions of roughly equal size, volume, and/or concentration. In an embodiment, splitting the sample into a plurality of portions includes separating the sample into physically and/or fluidically isolated portions or aliquots. In an embodiment, separating the sample includes separating the sample into a number of portions separately and individually disposed in individual wells, compartments, and the like, such as with portions of the sample individually disposed in wells of a multi-well plate. In an embodiment, separating the sample includes separating the sample into wells of a multi-well plate, where the multi-well plate comprises a number of wells selected from the group consisting of 2, 4, 8, 12, 16, 24, 32, 64, 96, 384, and 1536.

As above, in an embodiment, the methods of the present disclosure can begin with attaching a first nucleic acid molecule to target amino acid residues in the plurality of proteins in the sample to provide nascent nucleic acid tags at the target amino acid residues. However, in other embodiments, the method begins with other method steps, such as splitting the sample into a plurality of partitions. In such an embodiment, the method can further include attaching handles to the proteins disposed in the plurality of partitions. In this regard, an aliquot in a given partition has a unique identifier, which would make it possible to do one fewer round of split-pool barcoding.

Figure 6:
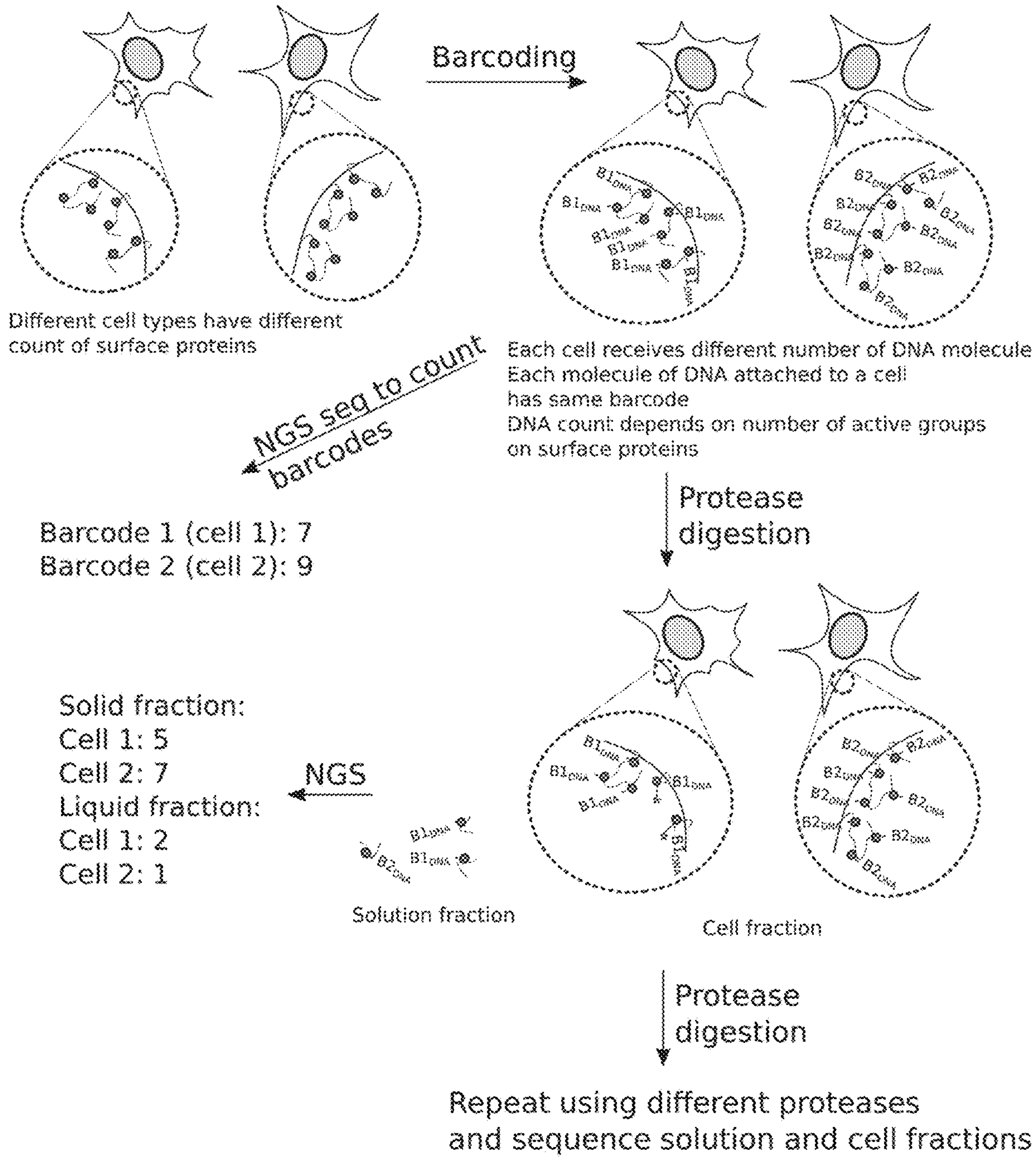
FIG. 6 schematically illustrates a method, according to an embodiment of the present disclosure, including combinatorially barcoding proteins disposed on a surface of cells.

In an embodiment, the sample comprises a plurality of cells and the plurality of proteins are disposed within and/or on the plurality of cells. In an embodiment, the portions or partitions are the cells themselves. In an embodiment, the cells are fixed, such as with formaldehyde, methanol, ethanol, acetic acid, or the like. In such an embodiment, splitting the sample includes separating cells of the plurality of cells from one another. FIG. 6 schematically illustrates a method, according to an embodiment of the present disclosure, including combinatorially barcoding proteins disposed on a surface of cells.

In the illustrated embodiment, two cells have different numbers of proteins disposed on surfaces of the cells. The surface proteins are barcoded, such as combinatorially barcoded with barcode nucleic acid molecules, discussed elsewhere herein. In this regard, individual cells are partitioned such that they receive a unique mature barcode as a result of the combinatorial barcoding process.

As shown, the cell surface proteins are subjected to protease digestion. In this regard, in a solution fraction, portions of labelled proteins are cleaved from the cells. The barcodes of these portions of proteins in the solution fraction are sequenced, such as through next generation sequencing (NGS). The remaining labelled proteins in the solid fraction, i.e., those that remain coupled to the cells, may also be sequenced. In the illustrated embodiment, the cells are subjected to a second round of protease digestion, such as with a different protease. Each of these protein digestion and sequencing steps may reveal structural and/or sequence information of the proteins on the cell surface, as discussed elsewhere herein.

While cells are described, it will be understood that cells, parts of cells, organelles, vesicles, and other aggregates and structures that contain proteins are also amenable to barcoding according to the methods of the present disclosure and are encompassed within the scope of the present disclosure.

As above, in an embodiment, the method includes ligating a barcode nucleic acid molecule to first nucleic acid molecules attached to the proteins, wherein the barcode nucleic acid molecule in each partition in the plurality of partitions comprise a barcode sequence unique to that partition. By ligating the barcode nucleic acid molecule to the first nucleic acid, the protein can be identified, at least in part, by the barcode nucleic acid, such as through sequencing the barcode sequence.

After ligation, the separate portions or aliquots are combined or pooled. Additionally, the process of splitting, labelling/ligating, and pooling can be repeated any number of times and, in so doing, the proteins, particularly, the target amino acid residues, are combinatorially labelled. In an embodiment, the split-pool barcoding is performed 2, 3, 4, 5, 6, 7, 8, 9, 10, or more times. In an embodiment, the number of times is selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, etc. In an embodiment, the number of times may be selected to provide a greater than 50% likelihood, greater than 90% likelihood, greater than 95% likelihood, greater than 99% likelihood, or some other probability that the target amino acid residues of a particular protein from the sample are uniquely labelled.

In an embodiment, the barcode nucleic acid comprises a sequence, such as a bridge sequence, complementary to a region on the nascent nucleic acid tag and/or other barcode nucleic acids. In this regard, the barcodes are configured to hybridize with the nascent nucleic acid tags from an initial labelling and barcode nucleic acid molecules from future rounds of split-pool barcoding.

An example of split-pool barcoding according to an embodiment of the present disclosure is illustrated in FIG. 1. In a first step, active groups, such as on target amino acid residues, are modified with a functional or active group. The modified proteins are split into different and separate partitions. Within the partitions, the proteins are labelled with different barcodes, shown here as barcode 1 and barcode 2. Once labelled, the proteins are pooled together, and then split into different partitions, here described as different wells. As shown, in the second round of labelling, different proteins are disposed in the first and second partitions than in the first round. The proteins, already once labelled, are labelled again with barcode 1 and barcode 2. Once pooled a second time, the proteins in the sample are uniquely combinatorially labelled, where such nucleic acid labels can be sequenced, as described further herein.

Particles

In an embodiment, the method includes immobilizing the plurality of proteins on a plurality of particles. In some instances, protein-nucleic acid complexes, such as those generated through split-pool barcoding, precipitate. In an embodiment, the proteins precipitate before they are labelled, or they precipitate during or after initial chemical attachment of nucleic acid molecules. To avoid such precipitation or its negative effects, the proteins are coupled, bound, or otherwise immobilized onto particles, such as beads. In this regard, certain such particles or beads are compatible with harsh conditions for DNA modification, which would otherwise cause protein precipitation.

The beads or particles can be any beads or particles suitable for binding to protein-nucleic acid complexes and/or proteins before coupling to nucleic acid molecules. In an embodiment, the particles are selected from the group consisting of metal particles, polymeric particles, sol-gel particles, glass beads, and combinations thereof. In an embodiment, the particles include magnetic particles, such as paramagnetic particles, ferromagnetic particles, superparamagnetic particles, and the like. In an embodiment, the particles include latex beads. In an embodiment, the particles include gold nanoparticles or other gold particles.

In an embodiment, the particles are monovalent particles. In this regard, in an embodiment, a single protein of the plurality of proteins is immobilized on a particle of the plurality of particles. By having one protein disposed on a single particle, the particle can be used to manipulate the single protein throughout the split-pool barcoding process. Were more than one protein irreversibly coupled to a single particle, the proteins coupled to the particle might be labelled with the same barcodes and, thus, be incorrectly indistinguishable on the basis of barcodes appended thereto. However, in certain embodiments, certain forms of Next Generation Sequencing can detect whether more than one protein is bound to a single bead.

Accordingly, in an embodiment, immobilizing the plurality of proteins on a plurality of particles comprises contacting the proteins in an excess of beads to ensure or strongly increase the likelihood that only a single protein is immobilized on a particle bead or particle. In an embodiment, particles of the plurality of particles have a number of reactive groups, but because of the excess of particles to proteins, most or all of the particles coupled to a protein have only a single protein coupled thereto.

Figure 3:
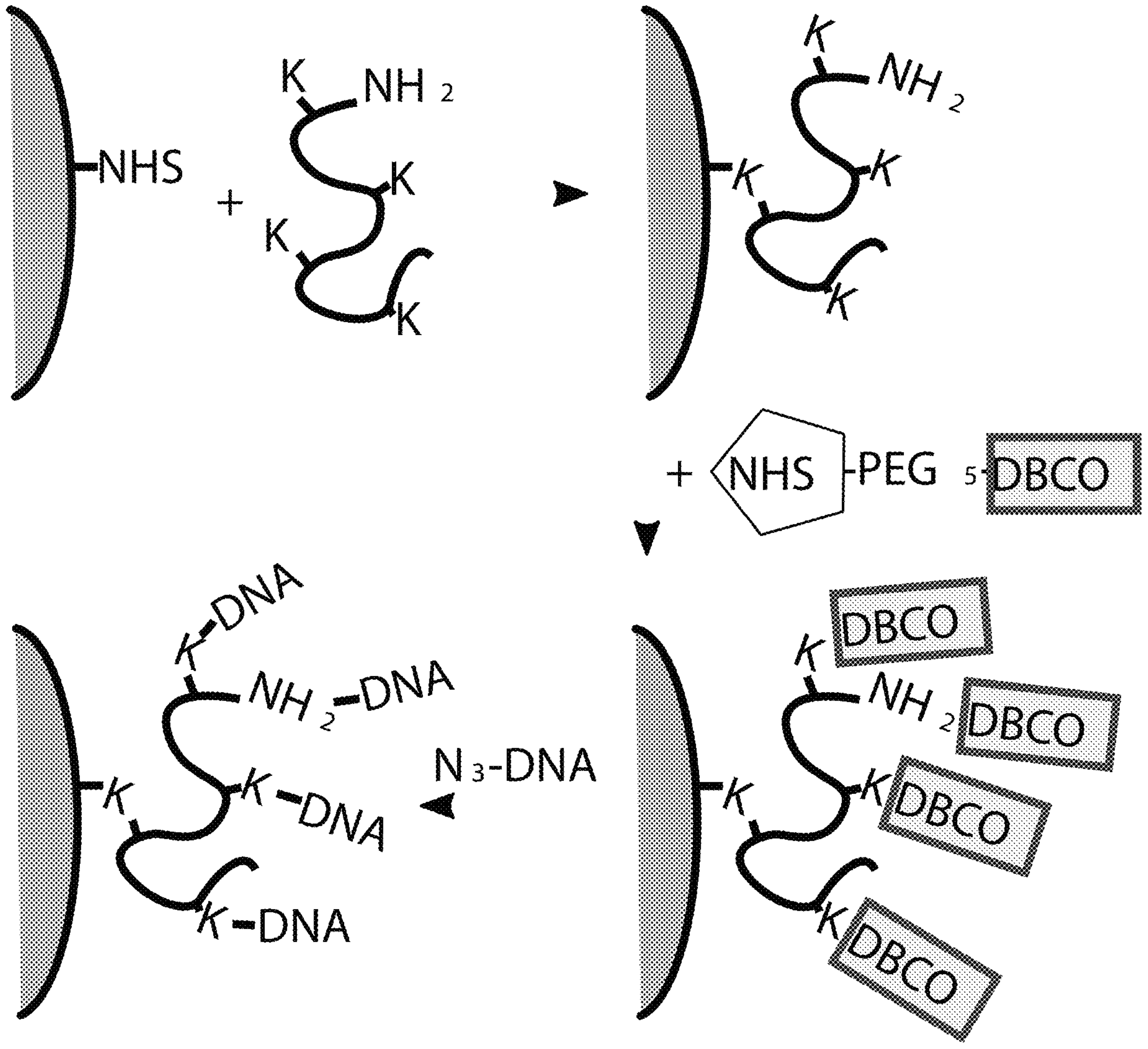
FIG. 3 schematically illustrates a method of immobilizing a protein on a particle and coupling functional groups to target amino acid residues of the protein, according to an embodiment of the present disclosure.

Proteins can be coupled to the particles through a number of positions and with a number of different reagents or structures. In an embodiment, the particle comprises a moiety or functional group configured to react with, such as through the formation of one or more chemical bonds, with the protein. In an embodiment, the particle includes one or more functional groups, such as an NHS group, configured to form a bond with a target amino acid residue, such as an amino acid residue comprising a reactive amine group. In an embodiment, immobilizing the plurality of proteins on the plurality of particles comprises coupling to a functional group on a particle of the plurality of particles to a target amino acid residue of a protein of the plurality of proteins. An example of such particle/protein coupling according to an embodiment of the present disclosure is schematically illustrated in FIG. 3. As shown, an NHS group on a particle is used to couple with an amine group on a protein. Remaining amine sidechain groups are then functionalized with a bifunctional linker, shown here including an NHS group and a DBCO group linked by a PEG linker. The DBCO groups are then coupled to an azide-functionalized nucleic acid molecule.

In an embodiment, the proteins are coupled to the particles through a terminal residue, such as through an N-terminal specific reaction. An advantage of using an N-terminal specific reaction for bead attachment is that all lysines remain available for attachment of DNA handles, thus eliminating a potential source of counting error. Further, in certain embodiments, such N-terminal reactions are reversible, and, accordingly, eliminate the need to ensure that only a single protein is attached to each bead: once bead-linked proteins are modified with DNA handles and have undergone some number of barcoding rounds, they can potentially be released and undergo one more split-barcode-pool cycle to ensure that each protein has a unique barcode.

In an embodiment, the method further includes washing the plurality of particles in denaturing conditions to remove non-covalently attached nucleic acid molecules from the plurality of particles. If not washed off, non-covalently attached nucleic acid molecules may be counted and mistaken for or conflated with barcode nucleic acid molecules. Such counted, non-covalently attached nucleic acid molecules could make accurately counting target amino acid residues more difficult or, perhaps, impossible.

While particles and beads are described to avoid or mitigate precipitation of nucleic acid-protein complexes, it will be understood that other approaches are contemplated and within the scope of the present disclosure. In an embodiment, the method includes chemically fusing proteins to poly(ethylene glycol)-(PEG)-like molecules to increase solubility. In an embodiment, the method includes chemically fusing proteins to long double-stranded DNA. In an embodiment, the method includes using other polymers of biological or artificial nature.

Proteolysis

As above, in certain embodiment, the methods of the present disclosure include cleavage, such as enzymatic cleavage, of the proteins in a sample. In embodiment, the methods of the present disclosure include subjecting the plurality of proteins in the sample to proteolysis prior to at least one of the one or more rounds of split-pool barcoding. By performing at least one round of split-pool barcoding after proteolysis or other enzymatic cleavage, additional structural detail may be gleaned from sequencing the barcodes, as discussed further herein.

In an embodiment, subjecting the plurality of proteins in the sample to proteolysis comprises contacting the sample with a protease configured to cleave a protein at a specific amino acid sequence. In this regard, the proteins are separated at a specific sequence and the two or more protein fragments, cleaved at the one or more specific sequences, are differently combinatorially barcoded after such cleavage.

Accordingly, in an embodiment, a first portion of the barcode in the two or more protein fragments will be common, whereas a second portion of the barcode, coupled to the protein fragments after the cleavage, will be different. See, for example, FIG. 2. By sequencing the barcodes of these protein fragments, it can be inferred that the protein fragments were once contiguous, thus providing structural information in addition to information that may be gleaned from counts of target amino acid residues.

In an embodiment, the method comprises contacting the sample with a protease prior to a plurality of rounds of split-pool barcoding, wherein the protease prior to each round of split-pool barcoding is different. As discussed further herein, by subjecting proteins to cleavage or other proteolysis and subsequently barcoding the proteins with one or more rounds of split-pool barcoding, additional structural or sequence information can be gleaned by comparing barcode nucleic acid sequences from before and after the cleavage. By cleaving the protein with different proteases that specifically cleave proteins at different amino acid sequences, additional protein sequence information may be generated. In this regard, the protein, which contains the two different amino acid sequences cleaved by the two different proteases, is split into several groups of sub-protein fragments cleaved at two or more different amino acid residue sequences. Because the proteins are subjected to split-pool barcoding after being cleaved by different sequence-specific proteases, the different sub-protein fragments are differently labelled after the cleavage. This means that the sub-protein fragments derived from a single intact protein will have barcodes that share a common first portion obtained prior to cleavage and different second portions obtained after cleavage. By sequencing these barcodes, it may be inferred that the sub-protein fragments were once part of a single intact protein, thus aiding in protein identification or fingerprinting.

The methods of the present disclosure can include subjecting the plurality of proteins in the sample to proteolysis or otherwise enzymatically cleaving the plurality of proteins with any protein suitable for such proteolysis and/or cleavage. In an embodiment, the proteins used for such proteolysis or cleavage include proteases, such as endoproteases. As discussed elsewhere herein, in an embodiment, the enzymes are configured to cleave the proteins at a specific amino acid sequence. In an embodiment, the endoprotease is selected from the group consisting of Granzyme B, all existing caspases, endokinase, factor Xa, proline endopeptidase, chymotrypsin, trypsin, pepsin, ArgC proteinase, AspN endopeptidase, Glutamyl endopeptidase, LysC protease, Neutrophil endopeptidase, Protesinase K, Staphylococcal peptidase I, Thermolysin, and combinations thereof. In an embodiment, enzymes configured to cleave proteins and configured for use in the methods of the present disclosure are selected from the group consisting of Granzyme_B, Caspase1, Caspase2, Caspase3, Caspase4, Caspase5, Caspase6, Caspase7, Caspase8, Caspase9, Caspase10, Enterokinase, Factor_Xa, Hydroxylamine, Proline_endopeptidase, PreScission_Protease, TEV, ThreeC, Furin, ArgC_proteinase, AspN_endopeptidase, BNPS_Skatole, Glutamyl_endopeptidase, LysC, Neutrophil_elastase, Staphylococcal_peptidase_I, Trypsin, Trypsin_assuming_K_Blocked, Cathepsin_L, Cathepsin_V, Cathepsin_K, Cathepsin_S, Cathepsin_F, Cathepsin_B, Papain, Bromelain, Chymotrypsin_high_spec, Proteinase_K, Thermolysin, Pepsin, LysC, and combinations thereof. In an embodiment, enzymes configured to cleave proteins and configured for use in the methods of the present disclosure are selected from the group consisting of GluC, TEV protease, Furin, LysC, Caspase 1, Proteinase K, Trypsin, Protease Xa, and combinations thereof.

While enzymatic protein cleavage is described, it will be understood that chemical cleavage (i.e., non-enzymatic cleavage) of proteins is within the scope of and encompassed within the methods of the present disclosure. In an embodiment, chemical cleavage agents suitable for use with the methods of the present disclosure include hydroxylamine, NTCB (2-nitro-5-thiocyanobenzoic acid), CNBr, formic acid, and combinations thereof.

Figure 2:
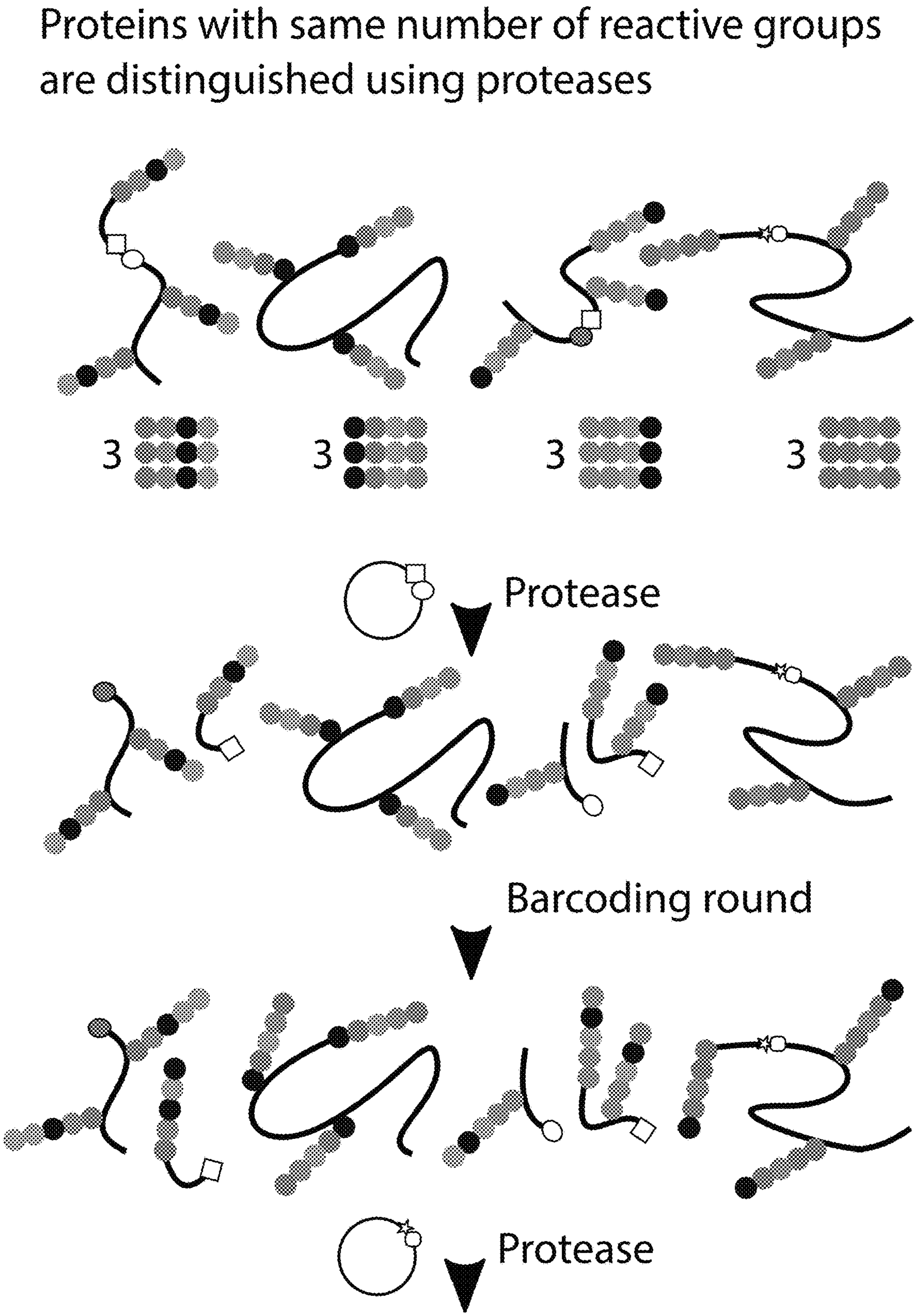
FIG. 2 schematically illustrates another method of combinatorially labelling proteins, according to an embodiment of the present disclosure.
Figure 2:
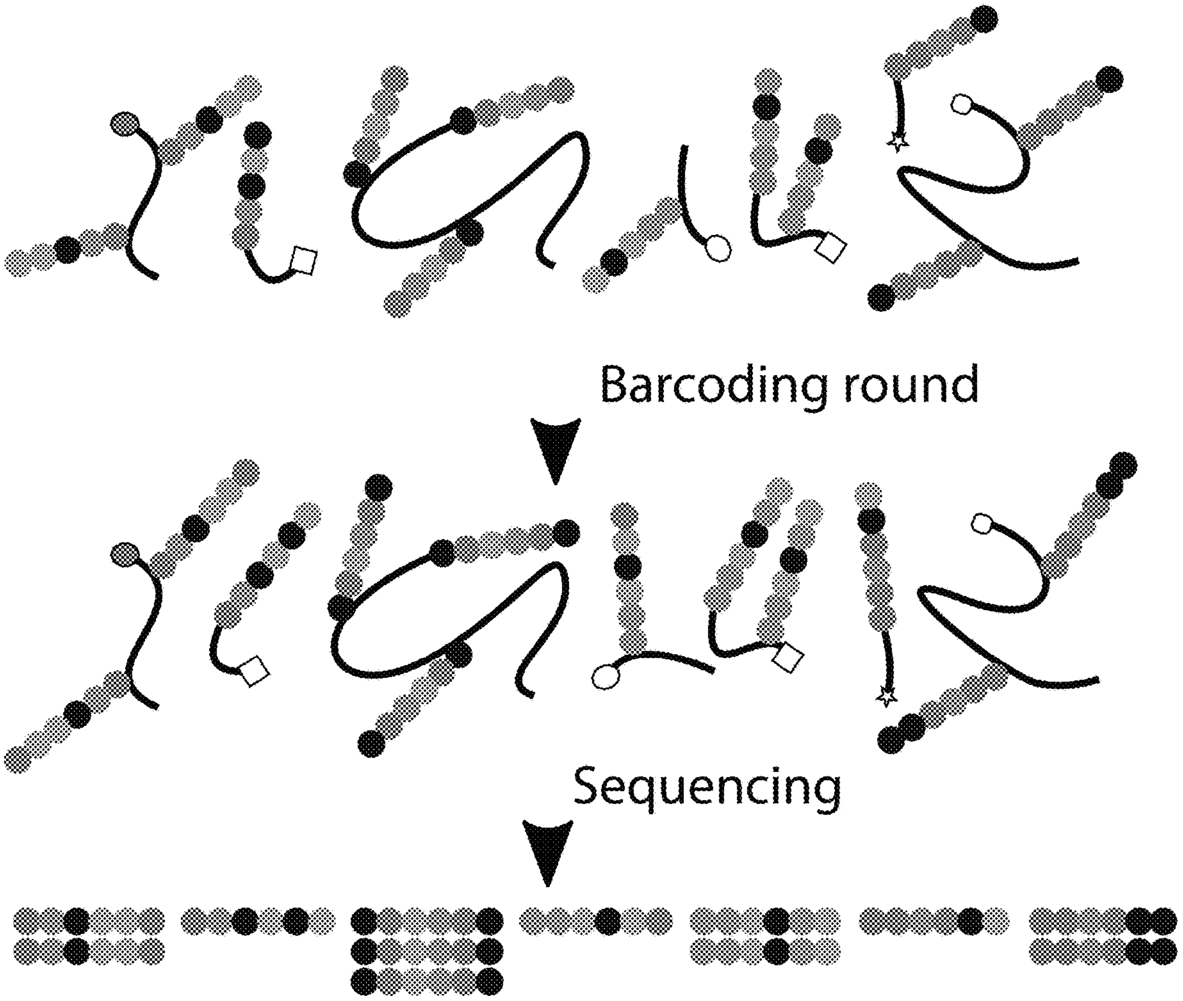
Figure 2:
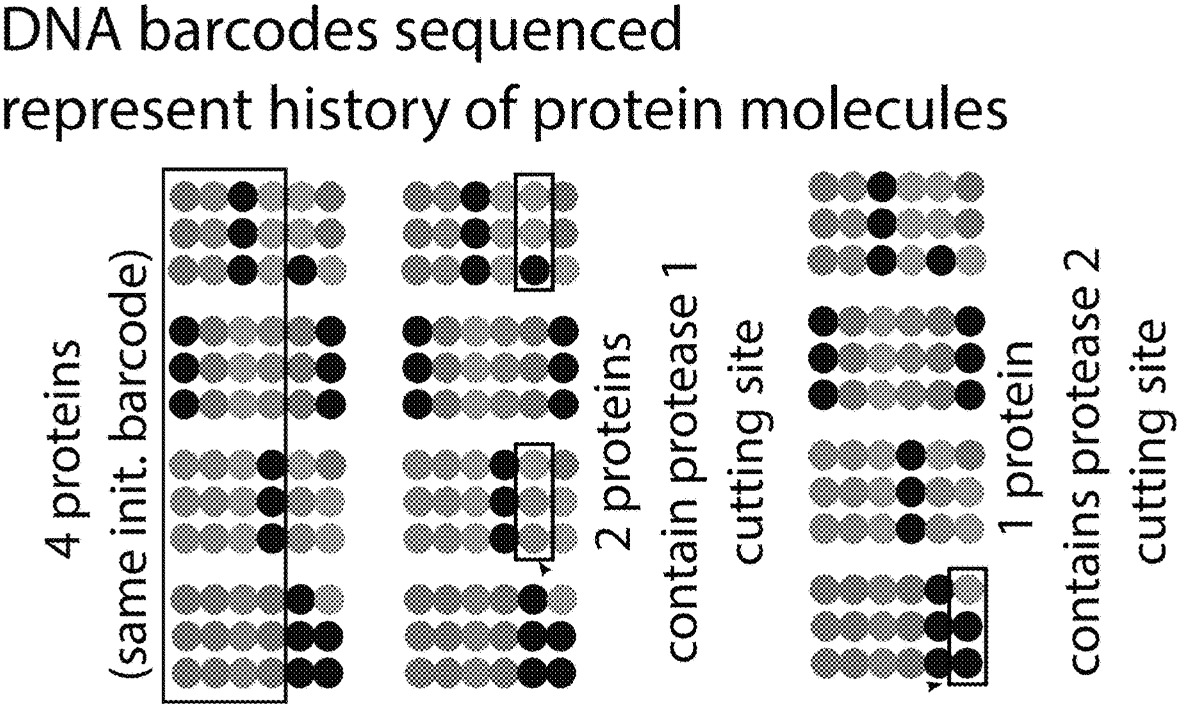

An example labelling, which includes proteolysis, according to an embodiment of the present disclosure, is schematically illustrated in FIG. 2, and will now be described. As shown, four different proteins have been combinatorially labelled, such as described further herein with respect to, for example, FIG. 1. As shown, three of the proteins include protease cutting sites. In the illustrated embodiment, the sample is contacted with a first protease configured to cleave proteins at a first amino acid sequence, which is included in two of the four proteins, shown cleaved in this first cleaving step. After a first cleaving step, the proteins and sub-protein fragments are subjected to a round of barcoding, such as a round of barcoding as described elsewhere herein in which a barcode nucleic acid molecule is appended to previously attached barcode nucleic acid molecules. After the post-proteolysis round of barcoding, the proteins and sub-protein fragments are subjected to a second round of proteolysis. In the illustrated embodiment, the proteins and sub-protein fragments are contacted with a second protease configured to cleave proteins at a second amino acid sequence, such as a second protease cutting site, which is included in another of the four proteins. As shown, this generates a second set of sub-protein fragments. After the second proteolysis step, the proteins and sub-protein fragments are subjected to another round of barcoding.

Still referring to FIG. 2, after the illustrated rounds of proteolysis, the barcodes are sequenced, such as described elsewhere herein. As shown, some of the sequenced barcodes include portions that are common, indicating proteins that were once contiguous, and other portions that are different, indicating that at some point in barcoding they were cleaved, such as at a protease cutting site. As described elsewhere herein, this information can be used to determine both a number of reactive sites, such as a number of target amino acid residues, and a number or presence of protease cutting sites.

Sequencing and Fingerprinting

As above, the methods of the present disclosure can include sequencing the mature nucleic acid tags. Such sequencing can include the use of any nucleic acid sequencing techniques, including but not limited to Sanger sequencing, next generation sequencing or other massively parallel sequencing methods, such as Illumina™ sequencing, and the like.

In an embodiment, the methods of the present disclosure are methods of assessing target amino acid residue number and/or frequency in the plurality of proteins. Accordingly, in an embodiment, determining the number and/or frequency of target amino acid residues in the one or more protein of the plurality of proteins is based on the barcode sequencing information. In this regard, where a target amino acid, such as a lysine, is barcoded through split-pool barcoding, determining the number and/or frequency of the target amino acid residues can include counting a number of barcodes having the same, or in some cases overlapping, barcode sequences. Because, in some embodiments, all labelled target amino acids in a single protein or sub-protein fragment are labelled with a common barcode, counting the number of such barcodes can provide information of the number of target amino acid residues contained on that protein or sub-protein fragment.

As discussed elsewhere herein, in an embodiment, the plurality of proteins is subjected to proteolysis prior to at least one of the one or more rounds of split-pool barcoding. Accordingly, sub-protein fragments generated from the proteolysis are barcoded after cleavage and, thus, the target amino acid residues of sub-protein fragments derived from a single intact protein will share a first barcode segment derived from split-pool barcoding prior to cleavage and target amino acid residues on the different sub-protein fragments will have a second barcode segment different from other sub-protein fragments that is derived from barcoding appended after cleavage. In such scenarios, the sequence information can be used to determine both the frequency or number of target amino acid residues in a protein and a number of amino acid sequences that are specifically cleaved by the enzyme(s) used for proteolysis.

In an embodiment, the methods of the present disclosure include generating identification data indicating an identity of the one or more proteins based on the number and/or frequency of target amino acid residues in the one or more protein of the plurality of proteins. In an embodiment, generating the identification data comprises comparing the frequency or number of target amino acid residues to known amino acid sequences. Based upon the number of target amino acid residues in a protein, it may be possible to uniquely identify a protein, such as where only a single protein contains such a particular number of target amino acid residues. In an embodiment, it may be possible to narrow the identity of the protein to a list or subset of proteins that contain the same number of target amino acid residues and, in this regard fingerprint the protein through partial sequence information. In an embodiment, the method includes correcting the number of target amino acid residues detected through barcoding and sequencing for any target amino acid residues that were used, for example, to couple the protein to a bead or particle. Such target amino acid residues used for coupling to a bead or particle may not be barcoded and, accordingly, a count of such target amino acid residues will undercount due to the coupling of a target amino acid residue to a bead or particle.

Figure 5A:
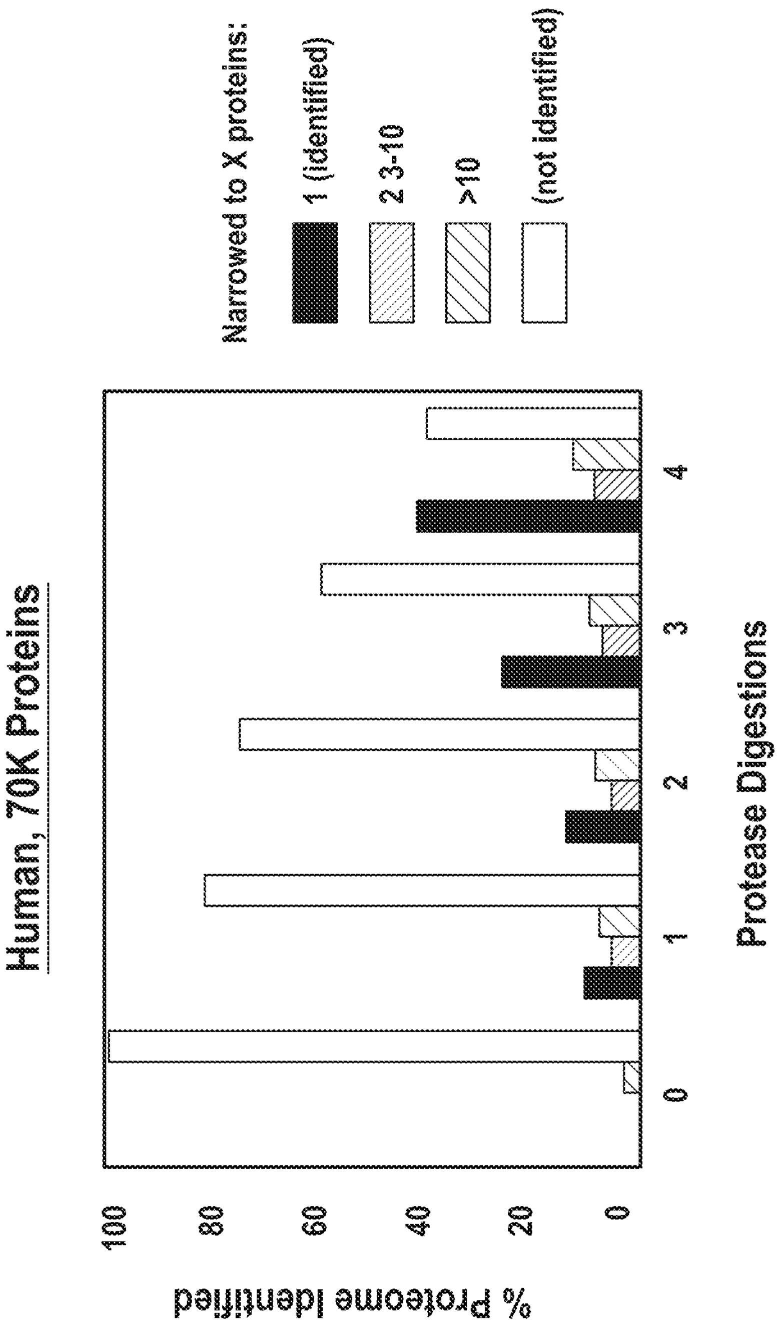
FIG. 5A graphically illustrates estimates of percentages of proteins in the human proteome that can be uniquely identified using methods according to embodiments of the present disclosure based on a number of protein digestions.
Figure 5B:
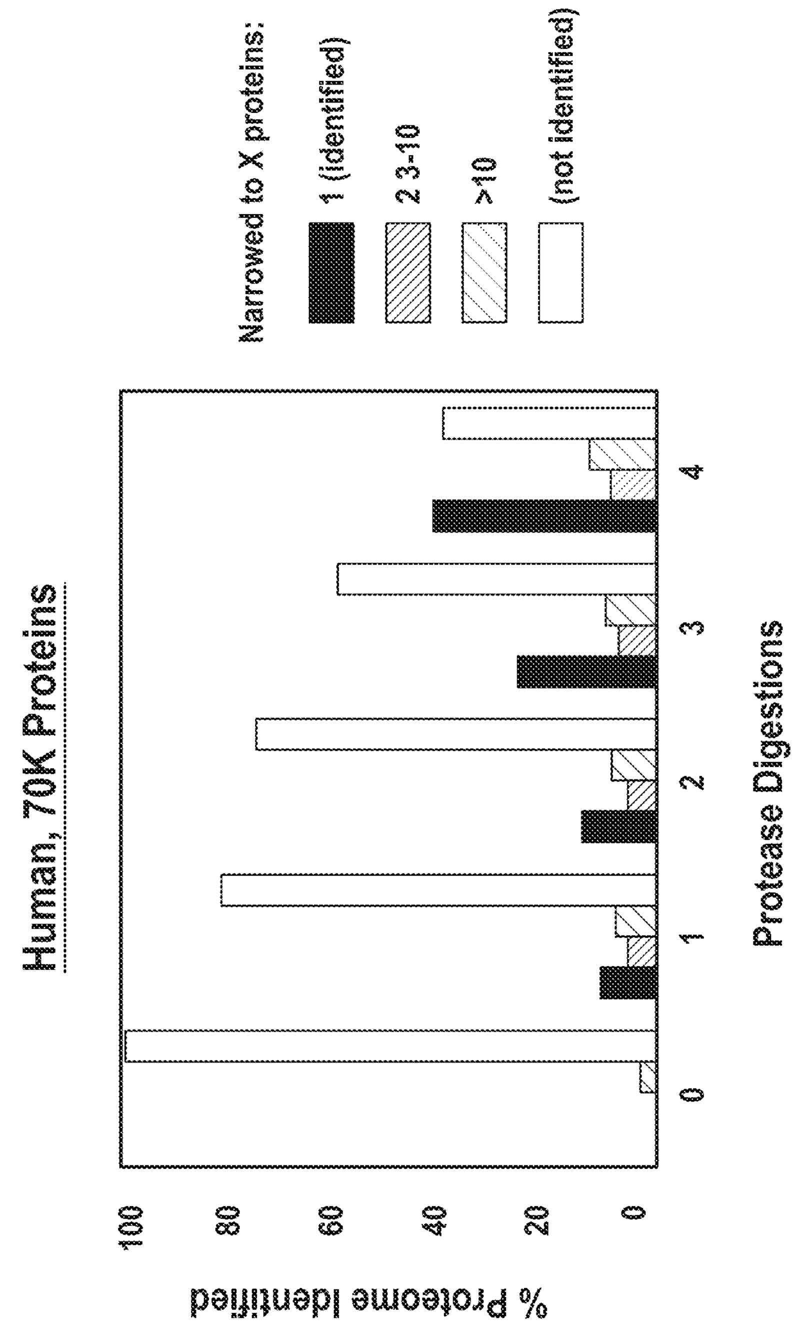
FIG. 5B graphically illustrates estimates of percentages of proteins in the yeast (*S. cerevisiae*) proteome that can be uniquely identified using methods according to embodiments of the present disclosure based on a number of protein digestions.
Figure 5C:
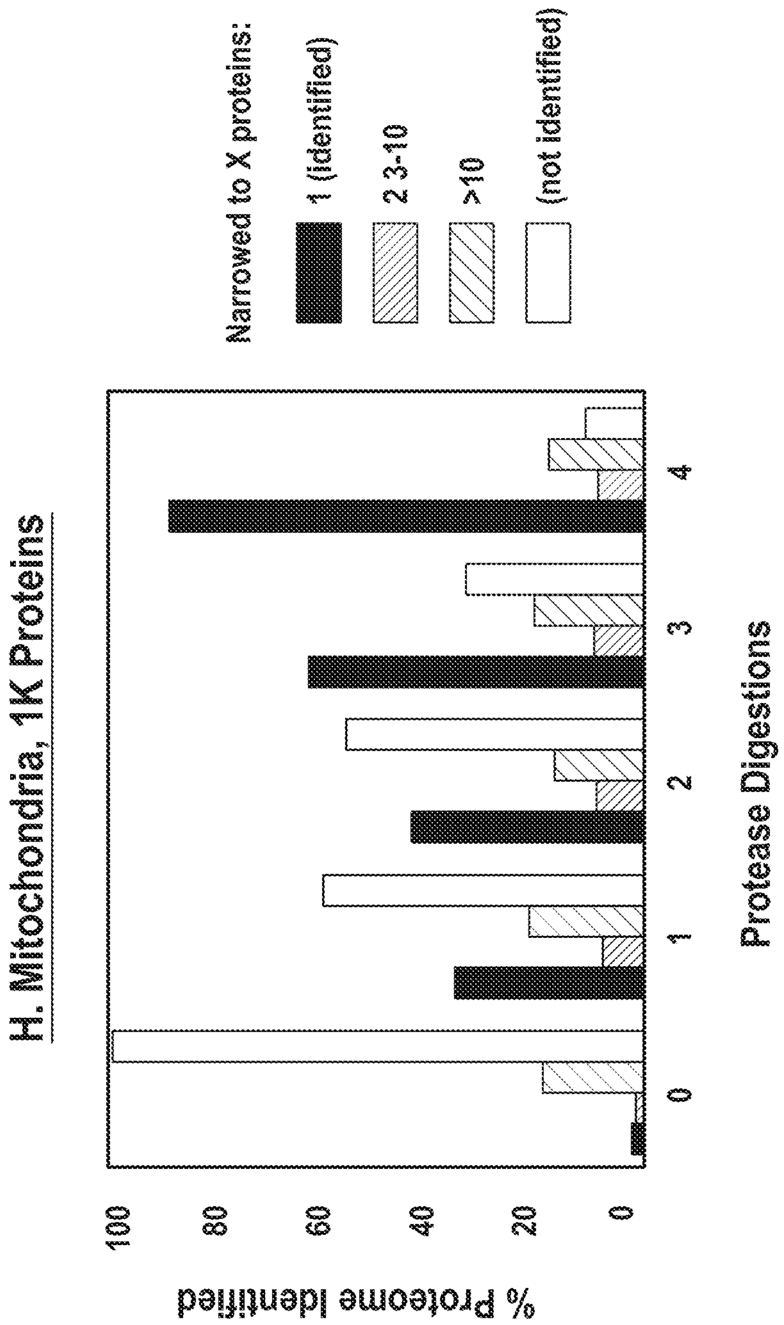
FIG. 5C graphically illustrates estimates of percentages of proteins in the human mitochondrial proteome that can be uniquely identified using methods according to embodiments of the present disclosure based on a number of protein digestions.

In an embodiment, generating the identification data comprises comparing barcode nucleic acid molecules ligated to the protein before and after proteolysis to generate cleavage information; and comparing the cleavage information to the known amino acid sequences. As discussed elsewhere herein, proteolysis or cleavage of the protein can provide additional protein sequence information, particularly where the cleavage is performed with an enzyme the cleaves proteins are specific amino acid sequences. In this regard, by comparing barcode nucleic acid molecules ligated to the protein before and after proteolysis to generate cleavage information, it is possible to determine or estimate the number of protein sequences in the protein that are cleaved by the protein used for proteolysis. This information and the frequency or number of target amino acid residues can be used to uniquely identify or narrow down possible protein identities. FIGS. 5A-5C graphically illustrate estimates of percentages of proteins in the human proteome (5A), the yeast (*S. cerevisiae*) (5B), and the human mitochondrial proteome (5C) that can be uniquely identified using methods according to embodiments of the present disclosure based on a number of protein digestions, exemplifying this sort of narrowing of protein identities.

The order in which some or all of the process steps are described should not be deemed limiting. Rather, one of ordinary skill in the art having the benefit of the present disclosure will understand that some of the process steps may be executed in a variety of orders not illustrated, or even in parallel.

In some embodiments, the processes explained above are described in terms of or may be implemented with computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

Accordingly, in an aspect, the present disclosure provides machine-readable storage media configured to perform one or more of the method steps described herein, such as when executed by a controller operatively coupled to hardware components. A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Kits

In another aspect, the present disclosure provides kits for assessing, analyzing, fingerprinting, and/or identifying proteins, such as proteins in a complex mixture or sample. In an embodiment, the kits are configured for and useful in performing one or more of the methods of the present disclosure.

In an embodiment, the kit comprises a functional group configured to couple with or covalently bind to a target amino acid residue; a first nucleic acid configured to react with and couple to the functional group; one or more barcode nucleic acid molecules configured to hybridize with, bind to, or otherwise couple with the first nucleic acids; and a chemical cleavage agent configured to cleave a protein.

In an embodiment, the kit comprises a functional group configured to couple with or covalently bind to a target amino acid residue. In an embodiment, the functional group is configured to bind with a reactive amine group. In an embodiment, the functional group comprises an NHS moiety configured to react and bind with an amine group of a target amino acid residue, such as lysine.

In an embodiment, kit comprises a first functional group configured to react with a first sidechain group of a first target amino acid; and a second functional group configured to react with a second sidechain group different than the first sidechain group of a second target amino acid residue different than the first target amino acid group. In this regard, in an embodiment, the first functional group and second functional group are configured to react in orthogonal reactions. In an embodiment, the first sidechain group comprises an amine group. In an embodiment, the second sidechain group comprises a carboxylic acid group or a thiol group.

In an embodiment, the functional group comprises a moiety or group configured to react with functionalized nucleic acid molecules, such those nucleic acid molecules comprising an azide group. In an embodiment, the functional group comprises a dibenzocyclooctyne group, such as a dibenzocyclooctyne group coupled to an NHS moiety through a linker. In an embodiment, the linker is a PEG linker.

In an embodiment, the kit further comprises a first nucleic acid configured to react with and couple to the functional group. In an embodiment, the first nucleic acid comprises an azide moiety configured to react with and couple to a dibenzocyclooctyne group.

In an embodiment, the kit further comprises one or more barcode nucleic acid molecules. In an embodiment, the barcode nucleic acid molecules are configured to hybridize with, bind to, or otherwise couple with the first nucleic acids, such as to form mature nucleic acid tags through one or more rounds of split-pool barcoding. In an embodiment, the barcode nucleic acid molecules include a bridge oligo complementary to the first nucleic acid molecule. In an embodiment, the barcode nucleic acid molecules include sequences complementary to the first nucleic acid molecule, as well as to other barcode nucleic acid molecules, so that barcode nucleic acid molecules can be coupled to the first nucleic acid molecule and subsequent barcode nucleic acid molecules in split-pool barcoding.

Additionally, in an embodiment, the kit can include sets of barcode nucleic acid molecules having barcode sequences that are different from barcode sequences of other sets of barcode nucleic acid molecules of the kit. Accordingly, in an embodiment, the kit may also comprise a plurality of first barcode nucleic acid molecules having a first barcode sequence and a second plurality of barcode nucleic acid molecules having a second barcode sequence different than the first barcode sequence.

In an embodiment, the kit may comprise at least one reverse transcription primer comprising a 5' overhang sequence. Each first barcode nucleic acid molecule may comprise a first strand. The first strand may include a 3' hybridization sequence extending from a 3' end of a first barcode sequence and a 5' hybridization sequence extending from a 5' end of the first barcode sequence. Each first barcode nucleic acid molecule may further comprise a second strand. The second strand may include an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence.

In an embodiment, the kit further comprises a plurality of second barcode nucleic acid molecules. Each second barcode nucleic acid molecules may comprise a first strand. The first strand may include a 3' hybridization sequence extending from a 3' end of a second barcode sequence and a 5' hybridization sequence extending from a 5' end of the second labeling sequence. Each second barcode nucleic acid molecules may further comprise a second strand. The second strand may comprise an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence. In some embodiments, the first barcode sequence may be different from the second barcode sequence.

In some embodiments, the kit may also comprise one or more additional pluralities of barcode nucleic acid molecules. Each barcode nucleic acid molecule of the one or more additional pluralities of barcode nucleic acid molecules may comprise a first strand. The first strand may include a 3' hybridization sequence extending from a 3' end of a barcode sequence and a 5' hybridization sequence extending from a 5' end of the barcode sequence. Each barcode nucleic acid molecule of the one or more additional pluralities of barcode nucleic acid molecules may also comprise a second strand. The second strand may include an overhang sequence, wherein the overhang sequence comprises (i) a first portion complementary to at least one of the 5' hybridization sequence and the 5' overhang sequence of the reverse transcription primer and (ii) a second portion complementary to the 3' hybridization sequence. In some embodiments, the barcode sequence may be different in each given additional plurality of barcode nucleic acid molecules.

In an embodiment, the kit comprises an enzyme, such as an enzyme configured to cleave a protein. In an embodiment, the enzyme is configured to cleave the protein through proteolysis. In an embodiment, the enzyme is a protease, such as an endoprotease. In an embodiment, the enzyme is configured to cleave the protein at a particular amino acid sequence, such as a first amino acid sequence. In an embodiment, the kit comprises a second enzyme configured to cleave a protein, such as a second enzyme configured to cleave a protein at a second amino acid sequence different than the first amino acid sequence. In an embodiment, the endoprotease is selected from the group consisting of Granzyme B, all existing caspases, endokinase, factor Xa, proline endopeptidase, chymotrypsin, trypsin, pepsin, ArgC proteinase, AspN endopeptidase, Glutamyl endopeptidase, LysC protease, Neutrophil endopeptidase, Protesinase K, Staphylococcal peptidase I, Thermolysin, and combinations thereof.

In an embodiment, the kit comprises a chemical cleavage agent. In an embodiment, the chemical cleavage agents are selected from the group consisting of hydroxylamine, NTCB (2-nitro-5-thiocyanobenzoic acid), CNBr, formic acid, and combinations thereof.

In an embodiment, the kit further comprises one or more beads or particles. In an embodiment, the beads/particles are functionalized to bind to or otherwise couple with a target amino acid residue. In an embodiment, the bead/particle is functionalized with an NHS group configured to bind to and react with amine group on a target amino acid residue.

In an embodiment, the bead/particle is functionalized with a single functional group, such as to couple with a single protein. As discussed further herein, it may be advantageous in certain embodiments to couple the bead/particle to a single protein, such as to avoid labelling more than one protein with the same set of barcode nucleic acid molecules.

In an embodiment, the particle is a magnetic particle. Such magnetic particles are generally easy to manipulate or maneuver, such as with other magnets. Additionally, magnetic particles are generally stable, inexpensive, and easy to count.

In an embodiment, the particle is a gold nanoparticle. In an embodiment, the gold nanoparticle is a monovalent gold nanoparticle comprising a single functional group configured to couple with a single protein.

In an embodiment, the particle is a latex particle, such as a fluorescently labelled latex particle.

In an embodiment, the kit further comprises a buffer or other liquid configured to wash non-covalently bound nucleic acid molecules from the particles.

In an embodiment, the kit further comprises a multi-well plate for partitioning a sample. In an embodiment, the multi-well plate comprises a number of wells selected from the group consisting of 2, 4, 8, 12, 16, 24, 32, 64, 96, 384, and 1536. In an embodiment, the kit comprises a plurality of vials or tubes, such as Eppendorf tubes, such as for partitioning a sample.

In an embodiment, the kit further comprises instructions for performing one or more methods of the present disclosure as described further herein.

EXAMPLES

Example 1: Split-Pool Barcoding to Determining Target Amino Acid Number

The present example demonstrates differentially barcoding two proteins in a mixture according to a method of the present disclosure and counting a number of target amino acid residues within each of these two proteins.

Figure 4:
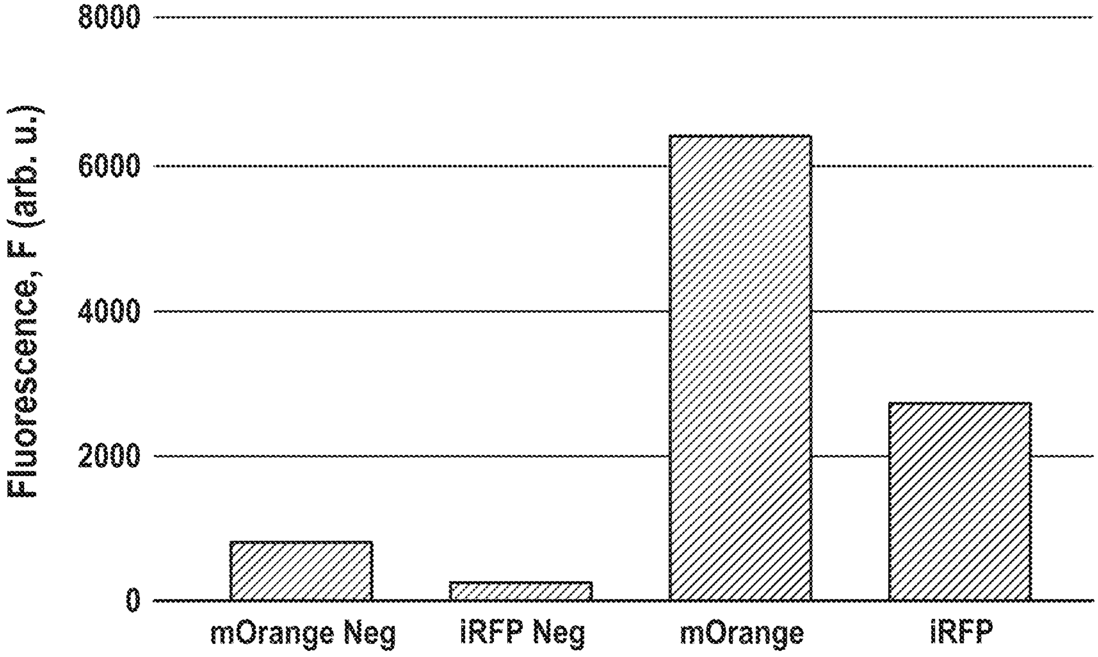
FIG. 4 graphically illustrates efficiency of attaching nucleic acid adaptors to two different proteins using fluorescence hybridization probes, in accordance with an embodiment of the present disclosure.

We coupled mOrange and iRFP to magnetic beads and then modified the remaining lysines with DNA handles. Specifically, we chose mOrange and iRFP because of the very different number of amine groups they carry and because of their distinct spectral properties, which are useful for quantification. mOrange contains 28 amines (27 lysines and an N-terminus), while iRFP has 5 amine groups. Under ideal conditions we thus expect to observe 5-6 times more DNA attached to mOrange than iRFP. We quantified the amount of DNA attached to proteins using fluorescence. Briefly, we hybridized a fluorophore-labelled DNA to the adapter attached to proteins. Then, we displaced the fluorescent DNA from the adapter, so the former stayed in solution. We separated beads from solution and quantitatively measured fluorescence of the solution. We observed that 2.5 times more fluorescent DNA was eluted from mOrange-modified beads than from iRFP-modified, again in accordance with the fact that mOrange has more binding sites than iRFP. We did not observe precise 28/5=5.6 times difference probably due to inefficiencies of this early-stage protocol. See FIG. 4.

Next, we performed three rounds of the split-pool barcoding. An example split-pool protocol will now be described. The first step in our barcoding workflow is the attachment of DNA handles to a specific type of residue. The labeling reaction is performed under denaturing conditions such that, ideally, all Lysine residues in the protein are modified.

In our preliminary study, we used amine-NHS click chemistry reactions to attach DNA adapters to proteins. While the reaction proceeds with high efficiency, we observed significant precipitation of protein-DNA complex as reported previously. To overcome this issue, we attached proteins to magnetic beads through amine-NHS chemistry. This procedure uses 1-2 amines on the protein to react with NHS groups immobilized on beads. Then, the remaining amines are modified with a commercially available NHS-PEG-DBCO heterobifunctional linker. Azide-modified DNA is reacted with DBCO group, resulting in covalent linkage between protein (immobilized on beads) and DNA. Magnetic beads greatly simplify manipulation of proteins in solution and are compatible with harsh conditions for DNA modification, which would otherwise cause protein precipitation. We use an excess of beads over proteins to ensure that only a single protein is attached per bead. An alternative is to use monovalent beads.

While coupling to target amino acid is described, it will be understood that it is also possible to couple a bead to a terminus of the protein, such as an N-terminus through an N-terminal specific reaction (see, e.g., MacDonald et al., 2015). This approach has already been applied for attachment of short peptides to beads to allow subsequent chemical modification of lysine and cysteine residues for fluorosequencing (Howard et al., 2020). An advantage of using an N-terminal specific reaction for bead attachment is that all lysines remain available for attachment of DNA handles, thus eliminating a potential source of counting error. An additional advantage of the attachment chemistry is that it is reversible. Reversibility eliminates the need to ensure that only a single protein is attached to each bead: once bead-linked proteins are modified with DNA handles and have undergone some number of barcoding rounds, they can potentially be released and undergo one more split-barcode-pool cycle to ensure that each protein has a unique barcode.

After this initial DNA-labeling of lysine residues, proteins are distributed into a set of wells, each containing a distinct DNA barcode sequence. Specifically, we will perform up to three rounds of barcoding with a total of three 96-well plates of barcode. First-round barcode oligos will be ligated on to the DNA handles on the lysine residues using a bridge oligo complementary to fixed regions within the handle and barcode. All proteins in a given well are barcoded with the same DNA sequence while proteins in different wells acquire different barcodes. Subsequently, proteins from all wells are pooled and distributed into a second set of wells containing a second set of barcodes. These second-round barcodes are then ligated on to the first-round barcode and this split, ligate, pool workflow is repeated. If N barcodes are used in M rounds for barcoding, a total of NM barcode combinations is generated. While we use three rounds of barcoding in 96 well plates for initial optimization experiments, it is possible to scale up to more rounds and potentially larger plate formats in the future. Additionally, it is possible to use a barcoding wherein two sets of barcodes ("A" and "B") are re-used repeatedly in an A-B-A-B- . . . pattern. This scheme has the potential advantage that is highly extensible at low cost. Assuming that the number of proteins in the mixture is much smaller than NM, it is very likely that each protein takes a unique path through the sequence of split-pool steps and will consequently acquire a unique barcode combination. Since each lysine residue on a given protein acquires the same barcode combination, the number of lysines on a protein can be determined by next generation sequencing of the barcodes.

The DNA from the barcoded beads was amplified and Sanger sequenced to confirm right configuration of the barcode. Sequencing clearly showed correct sequences for DNA adapters attached to proteins and for the constant linkers between barcodes. The actual 8 nt barcodes showed up as random sequences as expected for a mixture of sequences.

Finally, we performed Illumina high throughput sequencing on the resulting barcodes. We identified thousands of particles bearing barcodes each. On average, particles with proteins attached to them, bear 130-150 DNA barcodes, while control particles without protein carry 17 DNA barcodes.

Example 2: Split-Pool Barcoding with Proteolysis to Fingerprint and Identify Proteins in a Mixture Although the number of lysines (and/or cysteines) alone can be sufficient to identify proteins in a relatively simple mixture, additional steps will be required to uniquely identify each protein in a complex mixture such as a cellular proteome. To further narrow protein identity, we combine combinatorial barcoding with protease digestion as schematically illustrated in FIG. 2. Specifically, we first digest the entire protein mixture with a site-specific protease, followed by another round of DNA barcoding. After digestion, fragments derived from the same original protein will no longer travel together and the barcodes acquired after digestion will diverge. Still, from the barcodes acquired in the earlier rounds, it is possible to know which protein fragments belong together. From this step it is thus possible to infer how many protease sites are contained in each protein and where they lie with respect to the labeled lysine residues. This process can be repeated with a range of different proteases and protease cocktails to uniquely identify proteins even in a complex mixture.

After labelling lysines with DNA adapters and performing a number of barcoding rounds on a protein mixture, we digest the proteins mixture with a specific endoprotease or defined cocktail of proteases. The protease recognizes and cleaves specific amino acid sequence motifs. The protease digest thus produces n+1 protein fragments where n is number of protease cleavage sites in the original protein. All fragments derived from the same protein share a DNA barcode (assuming each fragment contains at least one lysine). After digestion, an additional barcoding step or steps is/are performed. This time, the DNA on each newly produced fragment likely receives a different barcode because those fragments are now independent molecules (Figure X). Before digestion, we only knew the total number of lysines per protein. The digestion and barcoding steps add two additional pieces of information. First, by counting how many unique barcodes appeared after the protease step, we can infer the number of protease sites in a protein. Moreover, by counting the number of DNA molecules with the same barcode added after protease digestion, we can learn how many lysines each new fragment has. This significantly refines the potential proteome space that a given protein can occupy.

We modeled the barcoding and protease digestion process on proteomes of different sizes (FIGS. 5A-5C). As expected, even in an ideal case where all amines in all proteins are modified with DNA handles, only a few proteins can be identified from target amino acid residue (e.g., lysine) counts alone. However, adding even one stage of protease digestion can dramatically increase the number of identified proteins.

Since we can repeat protease digestion and barcoding steps as many times as needed, more proteins will be identified after each round. For example, after four rounds of protease digestions followed by barcoding, it is theoretically possible to uniquely identify 90% of proteins in the human mitochondrial proteome which contains ~1000 proteins, close to 60% of proteins in the proteome of the yeast *S. cerevisiae* and 40% of proteins in the human proteome. In practice, no reaction step (DNA labeling, digestion, . . . ) step is perfectly efficient, which may introduce errors in protein identification.

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein, with respect to measurements, "about" means+/−5%.

The particulars shown herein are by way of example and for purposes of illustrative discussion of the preferred embodiments of the present disclosure only and are presented in the cause of providing what is to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While illustrative embodiments have been illustrated and described, it will be appreciated that various changes can be made therein without departing from the spirit and scope of the disclosure.

The invention claimed is:

1. A method of assessing target amino acid residue number in a plurality of proteins in a sample, comprising:

(a) attaching a first nucleic acid molecule to target amino acid residues in the plurality of proteins in the sample to provide nascent nucleic acid tags at the target amino acid residues;

(b) performing two or more rounds of split-pool barcoding to provide mature nucleic acid tags at the target amino acid residues, wherein the one or more rounds of split-pool barcoding comprise:

(i) splitting the sample into a plurality of partitions, (ii) ligating a barcode nucleic acid molecule to the first nucleic acid molecules attached to the proteins, wherein the barcode nucleic acid molecule in each partition in the plurality of partitions comprise a barcode sequence unique to that partition, and (iii) pooling the sample;

(c) sequencing the mature nucleic acid tags to generate barcode sequencing information; and (d) determining a number of the target amino acid residues, based on the barcode sequencing information, in one or more protein of the plurality of proteins.

2. The method of claim 1, further comprising subjecting the plurality of proteins in the sample to proteolysis prior to at least one of the one or more rounds of split-pool barcoding.

3. The method of claim 2, wherein subjecting the plurality of proteins in the sample to proteolysis comprises contacting the sample with a protease configured to cleave a protein at a specific amino acid sequence.

4. The method of claim 2, wherein the method comprises contacting the sample with a protease prior to a plurality of rounds of split-pool barcoding, wherein the protease prior to each round of split-pool barcoding is different.

5. The method of claim 1, wherein the target amino acid residues are selected from the group consisting of lysine, glutamic acid, aspartic acid, cysteine, arginine, histidine, tyrosine, and combinations thereof.

6. The method of claim 1, wherein the target nucleic acid resides comprise sidechain groups selected from the group consisting of an amine group, a carboxylic acid group, a thiol group, and combinations thereof.

7. The method of claim 1, wherein attaching the first nucleic acid molecule to the target amino acid residues in the plurality of proteins in the sample comprises:

coupling a functional group to the target amino acid residues, and coupling the first nucleic acid to the functional group.

8. The method of claim 7, wherein the target amino acid residues are first target amino acid residues comprising first sidechain groups and the functional group is a first functional group, wherein the method further comprises attaching a second nucleic acid molecule to second target amino acid residues different than the first target nucleic acid in the plurality of proteins in the sample.

9. The method of claim 8, wherein attaching a second nucleic acid molecule to second target amino acid residues comprises:

coupling a second functional group to the second target amino acid residues, and coupling the second nucleic acid to the second functional group.

10. The method of claim 9, wherein a reaction between the first functional group and the first target amino acid residues is orthogonal to a reaction between the second functional group and the second target amino acid residues.

11. The method of claim 1, wherein the proteins are denatured.

12. The method of claim 1, further comprising immobilizing the plurality of proteins on a plurality of particles.

13. The method of claim 12, wherein a single protein of the plurality of proteins is immobilized on a particle of the plurality of particles.

14. The method of claim 12, wherein immobilizing the plurality of proteins on the plurality of particles comprises coupling to a functional group on a particle of the plurality of particles to a target amino acid residue of a protein of the plurality of proteins.

15. The method of claim 12, wherein immobilizing the plurality of proteins on the particles comprises coupling a terminus of a protein of the plurality of proteins to a particle of the plurality of particles.

16. The method of claim 12, further comprising washing the plurality of particles in denaturing conditions to remove non-covalently attached nucleic acid molecules from the plurality of particles.

17. The method of claim 1, further comprising generating identification data indicating an identity of the one or more proteins based on the frequency of target amino acid residues in the one or more protein of the plurality of proteins, wherein generating the identification data comprises comparing the frequency of target amino acid residues to known amino acid sequences.

18. The method of claim 17, wherein generating the identification data comprises comparing barcode nucleic acid molecules ligated to the protein before and after proteolysis to generate cleavage information; and comparing the cleavage information to the known amino acid sequences.

19. A kit comprising:

a functional group configured to couple with or covalently bind to a target amino acid residue of a protein;

a first nucleic acid molecule configured to react with and couple to the functional group;

a plurality of first barcode nucleic acid molecules comprising a first barcode sequence configured to hybridize with, bind to, or otherwise couple with the first nucleic acids and other barcode nucleic acid molecules;

second plurality of barcode nucleic acid molecules configured to hybridize with, bind to, or otherwise couple with the first nucleic acids and other barcode nucleic acid molecules, the second plurality of barcode nucleic acid molecules comprising a second barcode sequence different than the first barcode sequence; and a chemical cleavage agent configured to cleave a protein.

20. The method of claim 1, wherein determining the number of the target amino acid residues comprises counting a number of barcodes having the same or overlapping barcode sequences.

* * * * *